United States Patent
Stender et al.

(10) Patent No.: US 8,051,414 B2
(45) Date of Patent: Nov. 1, 2011

(54) METHOD AND SYSTEM FOR REMOTE SOFTWARE UPDATING OF A MEDICAL DEVICE

(75) Inventors: Holger Stender, Ebermannstadt (DE); Klaus Gareis, Forchheim (DE); Reinhard Gebhardt, Erlangen (DE)

(73) Assignee: Siemens Aktiengesellschaft (DE)

( * ) Notice: Subject to any disclaimer, the term of this patent is extended or adjusted under 35 U.S.C. 154(b) by 1470 days.

(21) Appl. No.: 11/194,216

(22) Filed: Aug. 1, 2005

(65) Prior Publication Data
US 2007/0027506 A1 Feb. 1, 2007

(51) Int. Cl.
*G06F 9/44* (2006.01)
(52) U.S. Cl. ........................................................ 717/168
(58) Field of Classification Search ................... 717/168
See application file for complete search history.

(56) References Cited

U.S. PATENT DOCUMENTS

| 4,545,251 | A | | 10/1985 | Uchida et al. |
| 5,544,651 | A | | 8/1996 | Wilk |
| 5,603,323 | A | * | 2/1997 | Pflugrath et al. ............ 600/437 |
| 5,715,823 | A | | 2/1998 | Wood et al. |
| 5,851,186 | A | | 12/1998 | Wood et al. |
| 5,897,498 | A | | 4/1999 | Canfield et al. |
| 5,938,607 | A | | 8/1999 | Jago et al. |
| 6,524,245 | B1 | | 2/2003 | Rock et al. |
| 2001/0037220 | A1 | * | 11/2001 | Merry et al. ................... 705/3 |
| 2002/0077856 | A1 | * | 6/2002 | Pawlikowski et al. ........... 705/2 |
| 2004/0041839 | A1 | * | 3/2004 | Scher et al. ................... 345/772 |
| 2007/0027506 | A1 | * | 2/2007 | Stender et al. ................. 607/60 |

* cited by examiner

*Primary Examiner* — Philip Wang
(74) *Attorney, Agent, or Firm* — Lempia Summerfield Katz LLC (57) ABSTRACT

A system is provided comprising first, second, and third servers, a medical device, and a database storing a plurality of software updates for various medical devices. The second server stores software update history for medical devices located in a plurality of countries, and the third server is located in a country and stores software update history for medical devices located in that country. A request for a software update for a medical device is sent from the first server to the second server. The second server sends a command to the database, and the database sends the software update to the medical device. After an attempt has been made to install the software update in the medical device, the software update history for the medical device is automatically updated in the second and third servers.

12 Claims, 5 Drawing Sheets

METHOD AND SYSTEM FOR REMOTE SOFTWARE UPDATING OF A MEDICAL DEVICE

BACKGROUND

A software update for a medical device can be recorded on a data medium and physically brought to and installed on the medical device by a customer service engineer ("CSE") at a time arranged with the customer. This process of software updates can take a long time and, as such, may not be able to react to acute problems, such as gaps in security or technical problems, in adequate time. As a result, valuable time is lost in which the medical device is not used, thus entailing unnecessary costs for the customer. Further, this process can be expensive to both the medical device manufacturer and the customer. However, transmission of a software update to a medical device from a remote location is known. See U.S. Pat. Nos. 5,603,323 and 6,524,245.

Certain governments require that electronic records be kept of software updates to medical devices, both at a central location, such as a medical device manufacturer's facility, and in each country in which medical devices are located. Currently, the central server and the country-specific server are automatically notified when a software update of a medical device is needed. However, there is no automatic notification to the central server and the country-specific server after an attempt has been made to install the software update on the medical device.

SUMMARY

The present invention is defined by the following claims, and nothing in this section should be taken as a limitation on those claims.

By way of introduction, the below embodiments describe a method and system for remote software updating of a medical device. In one embodiment, a system is provided comprising first, second, and third servers, a medical device, and a database storing a plurality of software updates for various medical devices. The second server stores software update history for medical devices located in a plurality of countries, and the third server is located in a country and stores software update history for medical devices located in that country. In one presently preferred embodiment, a request for a software update for all medical devices of a type is sent from the first server to the second server. In that presently preferred embodiment, for the medical devices of that type that can be reached remotely, the second server sends a command to the database, and the database sends the software update to the medical device. After an attempt has been made to install the software update in the medical device, the software update history for the medical device is automatically updated in the second and third servers. Other embodiments are provided, and each of the embodiments described herein can be used alone or in combination with one another.

The embodiments will now be described with reference to the attached drawings.

DETAILED DESCRIPTION OF THE PRESENTLY PREFERRED EMBODIMENTS

By way of overview, the embodiments described below provide a method and system for remote software updating of a medical device. With these embodiments, software updates can be quickly provided to a medical device, helping to ensure that acute safety gaps can be reacted to quickly. Also, expense to both the medical device manufacturer and the customer can be reduced since medical device down time is minimized, and a CSE is no longer needed to physically transport a data medium containing the software update. Also, these embodiments can assure that, after the software update has been installed in the medical device, a record of the update is automatically stored in the appropriate locations, such as a central server and a country-specific server. Among the other advantages to these embodiments are: automated data flow, with resultant reduction in source of error and mistakes in data; better capability of documentation of software updates to authorities; equipment-specific shipping; reduction in travel times to various countries, resulting in reduction in cost and staffing losses by the medical device manufacturer; increasing productivity; and a fast reaction to problems, thus increasing system availability with attendant increased customer productivity. These embodiments may be especially easy to adopt in systems that already have an on-line connection to medical devices for preventive and curative monitoring.

Figure 1:
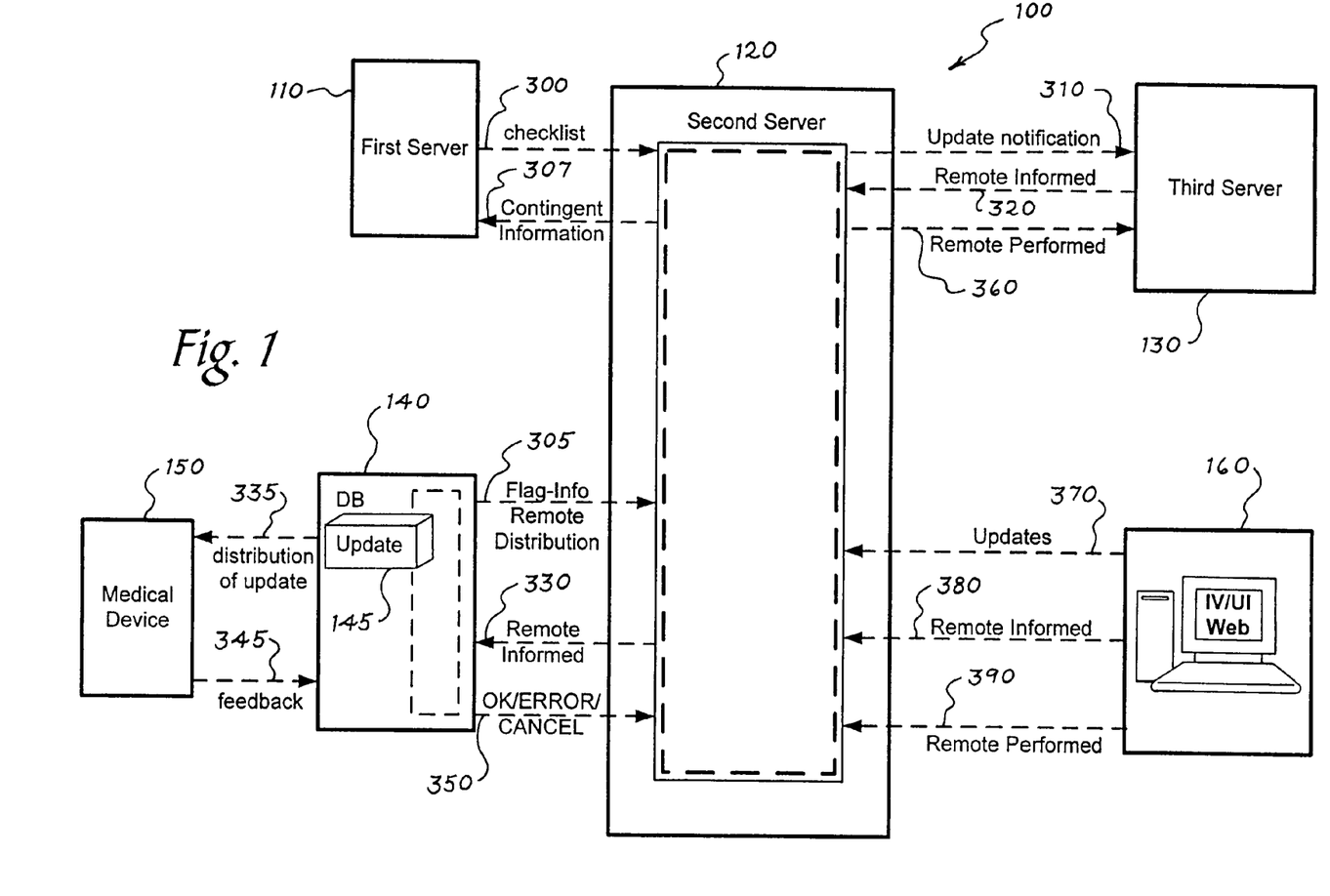
FIG. 1 is a block diagram of a system of a preferred embodiment.

Turning now to the drawings, FIG. 1 is an illustration of a system 100 of a preferred embodiment for remote software updating of a medical device. As shown in FIG. 1, this system 100 comprises a first server 110, a second server 120, a third server 130, a database ("DB") 140 storing a plurality of software updates (one of which is shown as update 145), and a plurality of medical devices (one of which is shown as medical device 150). The system 100 also comprises a computer 160 with web browsing software. In a presently preferred embodiment, the first server 110 contains information on the necessity of update on certain types of medical devices and on the necessary update kits "spare parts" for various medical devices, and the second server 120 contains information on various medical devices in various countries. For example, for a given type of medical device, the second server 120 can store information on where the different units of that type are located, what division the medical devices belong to, and an update history of each medical device. In a presently preferred embodiment, the second server 120 is located and maintained by the manufacturer of the medical devices. The third server 130 is located in a country and stores information (such as software update history) on medical devices located in that specific country. While only one "third server" is shown in FIG. 1, it should be understood that each country in which a medical device is located would have its own server storing information on the medical devices located in that country. The same applies to server 160 in case of non-SAP-countries.

In a presently preferred embodiment, the first server 110 is a server called SAP P41, the second server 120 is a server called SAP P42, the third server 130 is a server in an "SAP country", and the computer 160 is located in a "non-SAP country". SAP refers to Systems, Applications, and Products and is an enterprise resource planning software package that integrates a corporation's accounting, sales, distribution, manufacturing, planning, purchasing, human resources, analysis, and other transactions into one application. Certain governments require that electronic records be kept of software updates to medical devices, both at a central location, such as a medical device manufacturer's facility, and in each country in which medical devices are located. In this embodiment, the second server 120 is the central server, and the third server 130 is the country-specific server. In this way, the second server 120 contains centralized knowledge of the world-wide installed base of medical devices, while the third server 130 contains centralized knowledge of the country-wide installed base of medical devices. In this embodiment, a method is presented that not only performs a remote software update to a medical device but also automatically updates the software update history stored in the central server and the country-specific server, thereby ensuring that the governmental requirements are met. This method will be discussed in conjunction with the flow chart in FIG. 2 and the transactions shown in FIG. 1.

By way of background, at the start of the software updating process, a decision is made by the R&D department of the medical device manufacturer that a software update is needed for a medical device because of safety and/or performance and/or reliability reasons. As used herein, the term "software update" refers to computer-readable program code that will provide a medical device with functionality that it previously did not contain. The software update can pertain to any software entity on the medical device (e.g., operating system or higher-level application). For example, a software update can fix a security problem (e.g., a virus) or provide a medical device with imaging features previously not available on the device. Some types of updates require the involvement of a CSE while others do not. As used herein, a "category 1" or "pull" update is transferred from the DB server 140 to the medical device 150, initiated by a CSE, installed, and then reported back by the CSE. In contrast, a "category 2" or "push" update is transferred from DB server 140 to the medical device 150 initiated centrally by second server 120, installed, and reported back automatically without CSE involvement. With a "category 3" or "push with CSE" update, the update is transferred from the DB server 140 to the medical device 150, initiated centrally by second server 120, installed, and reported back by the CSE.

Figure 2:
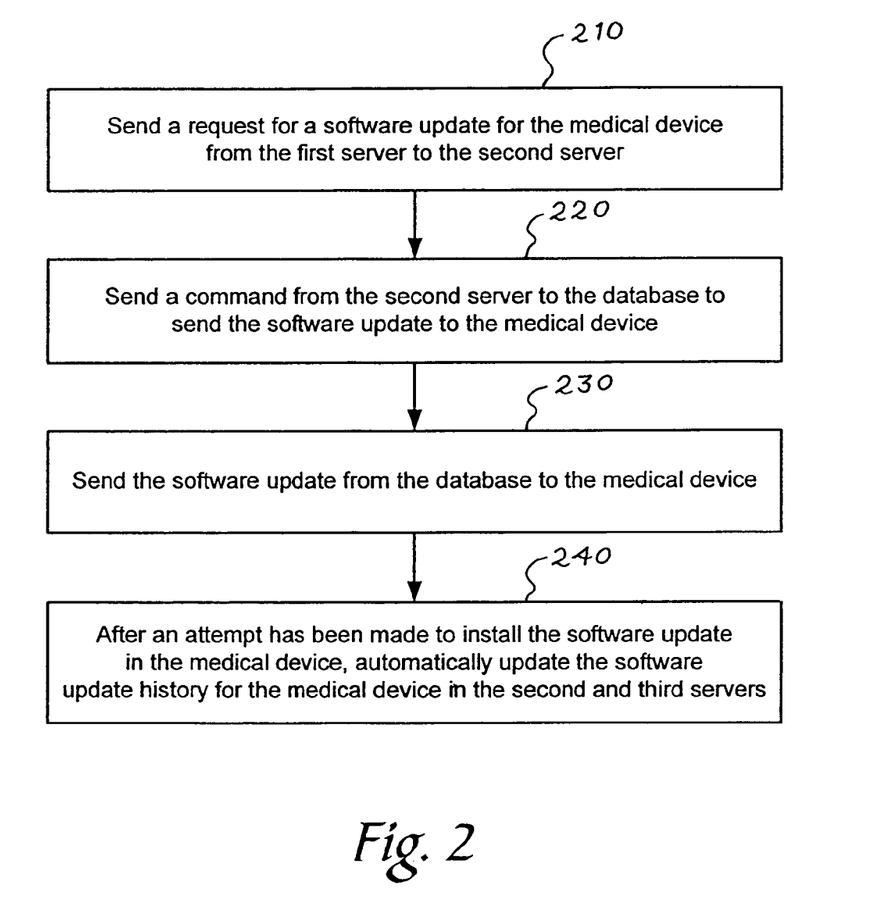
FIG. 2 is a flowchart of a method of a preferred embodiment.

Turning now to FIG. 2, the first server 110 sends a request (or "checklist") to the second server 120 for a software update (identified by an update number, for example) for all medical devices of a type (act 210 in FIG. 2 and transaction 300 in FIG. 1) with all the master data contained in a so called "checklist." The notification preferably includes a flag indicating that the update is a remote-capable update and indicates the category of the update (e.g., Category 1 or Category 2 or Category 3). Normally, instead of identifying a single medical device (by material no. and serial no.), the request can identify (by material no. and a group or range of serial nos.) a group or type of medical devices, and the second server 120, which stores information on which medical devices belong to various groups and where those medical devices are located, can determine which medical devices should get the update. Also, the second server 120 can identify for each device whether the type of update can be performed remotely. For example, some medical devices might not have the required set-up for a remote software update. Accordingly, it is preferred that the database 140 periodically send information (shows as the flag-info-remote-distribution transaction 305 in FIG. 1) to the second server 120 as to which medical devices can and cannot be remotely updated. As for those medical devices that cannot be remotely updated and for those updates that are not software updates, the second server 120 sends contingent information (see transaction 307 in FIG. 1) to the first server 110 to instruct the first server 110 how those medical devices should be updated (e.g., how many CD-ROMs will be needed to manually install the update).

Next, the second server 120 provides an update notification to the third server 130 (transaction 310), and the third server 130 sends a message back to the second server 120 to acknowledge receipt of the notification (the "remote informed" transaction 320). The second server 120 then sends a command to the database 140 to send the software update to the medical device 150 (act 220). This is shown by the "remote informed" message at transaction 330 in FIG. 1. Next, the software update 145 is sent from the database to the medical device 150 (act 230) (shown by the "distribution of update" transaction 335 in FIG. 1). After an attempt has been made to install the software update, feedback regarding the success of the installation is sent from the medical device 150 to the database 140 (transaction 345), and an ok/error/cancel message is sent from the database 140 to the second server 120 (transaction 350). In one presently preferred embodiment, the following information is sent to the second server 120: update number, material number, serial number of the medical device, date and time the remote update was started, date and time the remote update ended, and remote update status (e.g., OK, FAILED, or CANCEL). Subsequently, the software update history for the medical device 150 is automatically updated in the second and third servers 120, 130 (act 240) (the second server 120 is informed of the installation via transaction 350, and the third server 130 is informed of the installation via the remote performed transaction 360).

In one embodiment, the second and third servers 120, 130 are both SAP servers. If a country is not a SAP country, a computer 160 with a web browser can be used to access the second server 120. In operation, a user at the computer 160 would contact the second server 120 (instead of the second server 120 contacting the computer 160 as it does with the third server 130) to obtain update notifications and remote performed messages, as well as to send a remote informed message.

Even More Detailed Description of a Presently Preferred Embodiment

Figure 3:
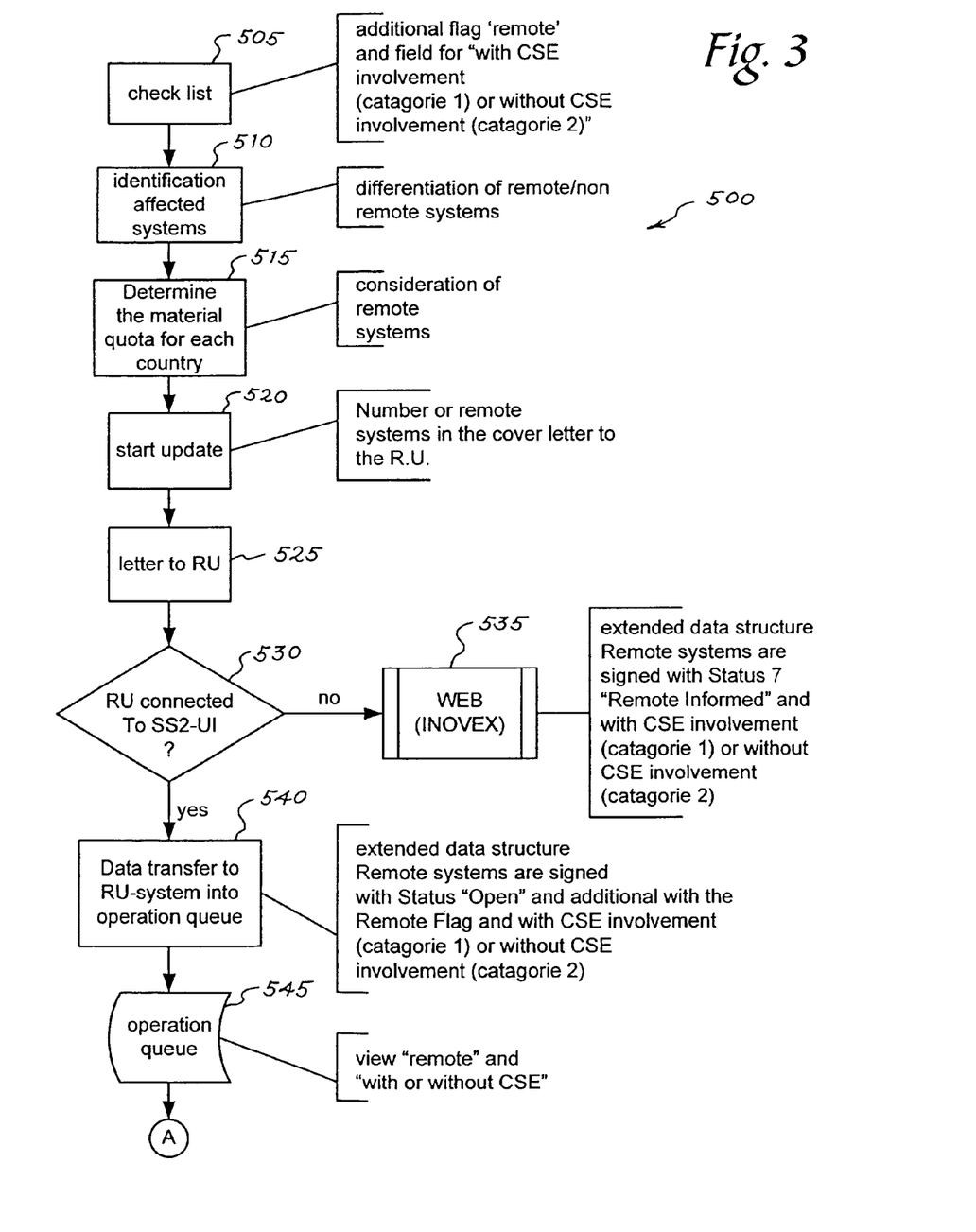
FIG. 3 is a flowchart of a method of a preferred embodiment.

Appendix I contains an even more detailed description of a presently preferred embodiment, and FIG. 3 is a flow chart 500 of a method for use with the embodiment described in the appendix. As shown in the flow chart 500, a check list is generated (act 505), and the affected systems are identified (act 510). After determining the material quota for each country (act 515), the update is started (act 520), and a letter is sent to the RU (act 525). A determination is then made as to whether the RU is connected to SS2-UI (act 530). If it is not, Web (Inovex) is performed (act 535). If it is, data is transferred to the RU-system into an operation queue (acts 540 and 545).

In the RU-system a determination is made regarding whether the system is a remote system (act 550). If it is not a remote system, a determination is made regarding whether notifications can bear the transferred standard nos. (act 555). If there is standard numbering, a notification is created with transferred standard no. and DISP task (act 560). If there is not standard numbering, transferred notification-no is converted (act 565), and a notification is created with converted no. and DISP task (act 570). In either case, the update is performed manually (act 575), the notification is closed (act 580), and acknowledgment is sent to the P42 server with the status (act 585). The method then ends (act 590).

If the system is a remote system, a determination is made regarding whether notifications can bear the transferred standard nos. (act 600). If there is standard numbering, a notification is created with transferred standard no. and a "remote informed" task (act 605). If there is not standard numbering, transferred notification-no is converted (act 610), and a notification is created with converted no. and the "remote informed" task (act 615). In either case, data is transferred to the P42 server (act 620), and data is transferred to the SDC (act 625). The remote update is then performed (act 630). A determination is then made as to whether the remove update was successful (act 635). If the remote update was successful, data is transferred to the P42 server with status 8 "Remote Performed" or status A "Remote Pending" (act 640) and then to RU into the operation queue (act 645). Next, a determination is then made as to whether there is a status A "Remote Pending" (act 647). If there is not, a determination is then made as to whether there is standard notification (act 650). (If there is a status A "Remote Pending," act 685 (described below) is performed.) If there is standard notification, the existing notification is closed (act 655), and the method ends (act 670). Otherwise, notification-No. is converted (act 660), and the existing notification is closed (act 665), and the method ends (act 670).

If the remote update was not successful, data is transferred to the P42 server (act 675) and to the RU into the operation queue (act 680). A determination is made regarding whether there is standard notification (act 685). If there is standard notification, a DISP task is created for existing notification (act 690). If there is not standard notification, notification-No is converted (act 695), and a DISP task is created for existing notification (act 700). In either case, the update is performed (act 705), the notification is closed (act 710), and acknowledgment is sent to the P42 server with the status (act 7155). The method then ends (act 720).

It should be noted that the above-described functionality can be implemented using any appropriate hardware and/or software component. In one embodiment, the functionality is implemented on an article of manufacture comprising a computer-readable storage medium and computer-readable data stored therein. Examples of the article include, but are not limited to, an electronic storage medium having electronic data, a magnetic storage medium having magnetic data, and an optical storage medium having optical data. Also, as used herein, the phrase "a server operative to" perform a function means that a single server can be used to perform the function, or two or more servers can be used to perform the function.

Lastly, it should be noted that the term "medical device" is intended to broadly cover any medical device, including, but not limited to, medical imaging devices, such as ultrasound imaging systems and those that use any of the following imaging modalities: computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy.

It is intended that the foregoing detailed description be understood as an illustration of selected forms that the invention can take and not as a definition of the invention. It is only the following claims, including all equivalents, that are intended to define the scope of this invention.

APPENDIX I

1 Scope of Application and Purpose

With the increased on-line connection of customer systems to Med CS for the sake of preventive and curative monitoring, there is also the chance of developing updates via this connection, if they comprise a software update.

In this section, the preferred requirements made of the methods involved will be described, so that the remote update process can be integrated with the general update process between the originating Med section and with the countries. As a result, updates can be developed more inexpensively, faster, and more reliably.

3.1 Definitions

"Category 1": Pull with CSE action ((the update is transferred by CSE from a central server to the system, installed, and reported back by CSE).

"Category 2": Push without CSE action (the update is transferred centrally from SDC to the systems, installed, and reported back automatically).

"Category 3": Push with CSE action (the update is transferred centrally from SDC to the systems, installed by CSE, and reported back).

"Remote Distribution" Flag: Identifies an Equi which has an agent for software distribution.

"Remote-capable Update" Flag: Identifies the update that can be remote-distributed.

5 Description of Functions 5.1 Overview

Into the existing combination method from P41 (P51), P42 and country SAP systems and the web application IV/UI, the SM-DB is incorporated as a further method involved; it is from the SM-DB that the remote updates are performed in the final analysis. This method is preferably annexed via new interfaces.

Since in remote updates the country organization remains in the information stream (in Category 1 and 3 updates, a CSE is preferably be on site; in Category 2 updates, the country is preferably informed), the existing programs and interface definitions are preferably expanded.

5.2 Wanted Functions

Below, the wanted functions required in the individual systems involved are described, including the interfaces between them. The systems involved are:

SAP P42 as the system for central initiation of updates and distribution to the countries Pseudo-system P42 LT (country template 3r42LT004) standing for SAP systems of the countries for performing the updates.

SM-DB as data base or application for administration of the connecting systems and the data associated with this.

Web application IV/UI for performing the update in non-SAP countries 5.2.1 Demands made of P42

5.2.1.1 Check List

The Service Notification that represents the update preferably includes a flag saying "Remote-capable Update" or the like that is visible in the dialog. The category of the update is preferably also distinguishable; Category 1 updates require CSE action on site; the remote update is then initiated by CSE (pull principle). Category 2 updates do not require CSE action; they are performed by the push principle. The country, however, is informed of their being performed. If the update is transferred from P41, both of these fields are preferably included. Updates of Category 3: the software is rewritten by the push method to the systems to be updated. Next, a CSE action is performed for installing the software on the customer's system.

5.2.1.2 Equipment Search

Upon selection ("Equipment Search" button) of a update that is remote-capable ("Remote-capable Update" flag), for each Equi (main or subsidiary equipment), the "Remote Distribution" flag is preferably taken into account. (This flag is implemented via a separate CR to P42 (137 112).) In the selection hit list, in the equipment totals per debitor and overall additionally as a subtraction set, the number of remote-capable pieces of equipment is preferably shown. If these subsets are shown in detail with the "Show Equipments" button, then the "Remote Distribution" flag is preferably shown for the pieces of equipment as well.

5.2.1.3 Start Update Process

The actions executed on starting the update process ("Start Update Process" button), for remote-capable updates and pieces of equipment, are preferably designed with the "Remote Distribution" flag as follows:

The update notification in P42 (type UI) is applied as before, with the status "open"; the data set sent to the country SAP system is assigned an additional code, "remote-capable." The two new flags in the update itself (see above) are also preferably be sent with this.

The entry in the UHDALL table is not changed.

5.2.1.4 Create Letter

In the "Material Text" field, two text modules are preferably appended for selection by hand:
 "This is a mixed update (remote and non-remote), so the material will be stocked only for the non-remote systems."
 "This is a remote update, so no material will be stocked."

In the "Reporting Text" field, one text module is preferably appended:
 "The remote update for connected systems will be automatically performed from the central SDC and reported in SAP or Intranet/eXtranet."

5.2.1.5 Update Letter

In the update letter, under "affected systems", the number of pieces of remote-capable equipment (reference: "Remote Distribution" flag!) of the update is preferably shown separately.

The two flags of the update should also be listed.

5.2.1.6 Interface with P41 for Making Update Kits Contingent

In transferring the data on a update to P41 for making it contingent and keeping the update kits in stock, the additional code "remote-capable" is preferably listed in the data set for each piece of equipment, and documentation is preferably provided that the update is remote-capable, if so, and that the Equi has the "Remote Distribution" flag.

5.2.1.7 Feedback Reports from the Country System

If a status 7 (REMOTE INFORMED) feedback report (see 5.2.2.3) comes from the country system, this status is continued in the UHDALL.

5.2.1.8 Transfer of Remote Informed to the SM-DB

In a daily file transfer (OPENFT), all the update jobs that have been reported back from the country to P42 as status 7 (in countries with and SAP interface) or in which the status 7 was just then set (web application IV/UI) are transferred to the SM-DB. This is done on the net principle; that is, only the change from the previous run is ever transferred. For monitoring purposes, the number of data sets that contain the data file is written in the first line of the data file. In every line after than, the following information per notification in status 7 is transferred:

Update No. Category (1 or 2 or 3) of the remote update, material no./serial no. of the equipment, UHDALL status ("7"), Date of the status, Country code (alpha2 code, such as DE, AT, US), Equi No.

5.2.1.9 Acceptance of Remote Update Feedback Reports from SM-DB

The feedback reports on the remote update activities taken over from the SM-DB are to be incorporated in P42. Feedback reports with the status "OK" (see 5.2.3.3) lead in Category 2 updates to a change in the status of the update notification in the UHDALL from "7" to "8" (REMOTE PERFORMED). This status matches the former status "1" (PERFORMED) in the sense that no further feedback report is expected. In remote updates of Category 3, the status of the update notification is converted in the table /SIEMEDTD/UHDALL from "7" to "A" (REMOTE PENDING).

Feedback reports whose status is "ERROR" (see 5.2.3.3) lead to a change in status of the update notification in the UHDALL from "7" (REMOTE INFORMED) to "9" (REMOTE FAILED). Such cases are preferably reported in an e-mail to the person responsible for updates in the country.

Feedback reports whose status is "CANCEL" (see 5.2.3.3) lead to a change in status of the update notification in the UHDALL from "7" to "5" (REMOTE REFUSED). Such cases are preferably reported in an e-mail to the person responsible for updates in the country.

5.2.1.10 Forwarding Remote Update Feedback Reports to the SAP Country

From the processing of the feedback reports taken over from the SM-DB, after the processing in P42, the corresponding processing is preferably initiated directly in the particular country SAP system. A distinction is preferably made whether the feedback report was positive or negative (status "OK" or "ERROR" vs. "CANCEL". See 5.2.2.4.

5.2.1.11 Adapting Status Administration in UHDALL about Equipment Changes ("Trigger")

The administration of the UHDALL status of update notifications from equipment changes are preferably changed so that the new status "8" is handled like former status "1", the new statuses "7," "9," and "A" are handled like former status "open", and the new status "5" is handled like former status "3" (CUSTOMER REFUSED).

5.2.1.12 Adapting Function Modules for P42 Access from Web Application "IV/UI"

The function modules for the P42 access from the web application "IV/UI" is preferably be adapted as follows:

The "remote-capable" and category ("1," "2," "3") or flags in the update, and the "Remote Distribution" flag on the equipment are preferably assessed.

The new UHDALL status "5", "7", "8" and "9" are preferably legible.

The UHDALL status is preferably capable of being changed from "open" to "7" (after the initial access by the person tasked with the update).

The UHDALL status "9" like the status "open" is preferably be capable of being changed to the status "1," "2," "3." It preferably must not be allowed to be set to "open," "4," "6," "7," "8," "9," or "A.".

The UHDALL status "A", like the status "open" is preferably capable of being changed to the status "1," "2," "3." It preferably must not be capable of being changed to "open," "4," "5," "6," "7," "8," or "9."

The UHDALL status "5" like the status "open" is preferably capable of being changed to the status "1," "2," "3." It preferably must not be allowed to be set to "open," "4," "6," "7," "8," "9."

5.2.2 Demands made of P42 LT 5.2.2.1 Interface with P42

The function modules for takeover of the data from P42 should be expanded with the fields names in 5.2.1.3.

5.2.2.2 Construction of Update Notifications

Data sets for a update that have been sent to an SAP country are automatically, depending on the parameter setting, constructed as update notifications, or arrive in a holding area from which they are then to be released. The notifications are then not created until release.

The triggering of the two alternatives should be change so that the update notifications are constructed automatically under the following preconditions:

Update is remote-capable

Update is Category 2 or 3

Data set for the equipment includes the "remote-capable" code.

5.2.2.2.1 Automatically Generated Update Notifications

If the update is remote-capable and has Category 2 (see 5.2.2.1) and the data set transferred from P42 for the equipment includes the "remote-capable" code (see above), then as before, a report is initiated, but instead of a DISP or WAIT action, a "REMOTE INFORMED" action is initiated.

If the update is remote-capable and has Category 1 (see 5.2.1.1), and the data set for the equipment, transferred from P42, has the "remote-capable" code, then as before a report with DISP action is initiated, but not an order.

If the update is remote-capable and has Category 3 (see 5.2.1.1), and the data set for the equipment, transferred from P42, has the "remote-capable" code (see above), a report is initiated as before, but instead of a DISP or a WAIT action, a "REMOTE INFORMED" action is initiated. No order is initiated.

Otherwise (no remote-capable update or non-remote-capable Equi), the procedure is the same as before.

5.2.2.2.2 Update Notifications Via a Holding Area

The two flags for the update are to be fitted into the view for the general data on a update at the header level (see 5.2.1.1).

For each equipment data set, the additional code "remote-capable" (see 5.2.1.3) is preferably fitted into the detail view. The "Create Notification" button converts marked entries from the list illustration that contain the "remote-capable" code into: a notification with a disp action, but not into an order.

Note: according to 5.2.2.2, this involves only Category 1 remote updates.

Other marked Equis are converted, as before, into a report and an order.

5.2.2.3 User Exit to the Report

In storing changes to the report in memory, the following changes are preferably made:

Notifications of the MU released with a "REMOTE INFORMED" action lead to feedback reporting a corresponding data set to P42 analogously to previous feedback report sets of status "7" (REMOTE INFORMED).

Notifications of the MU type released with a "REMOTE PERFORMED" do not lead to any feedback report of a corresponding data set to P42 (see 5.2.1.9). However, if the notification has an entry in the field headed "new software status reached", then the functionality to update the equipment is preferably performed with the new software status. This function is implemented simultaneously via another CR.

5.2.2.4 Followup Processing of Remote Update Feedback Reports from P42 or the SM-DB A function module is preferably provided that can be called up from P42 by RFC and that, depending on the feedback report transferred (positive or negative, status "OK", "ERROR", or "CANCEL"; see 5.2.1.10), takes various administrative actions.

5.2.2.4.1 Positive Feedback Report

Remote updates, Category 2: Notifications with status "8" in the UHDALL lead, in the country SAP, to completion of the REMOTE INFORMED action and construction of a REMOTE PERFORMED action. This action is immediately changed in status from "open" to "completed".

Remote updates, Category 3: Notifications of status "A" in the UHDALL lead in the country SAP to a completion of the REMOTE INFORMED action and for the construction of a DISP action with the short caption "Remote update pending" and the long caption "Remote update pending. Send CSE for installing."

5.2.2.4.2 Negative Feedback Report, Status 9

Notifications with status "9" in the UHDALL lead, in the country SAP, to completion of the REMOTE INFORMED action and construction of a DISP action. In the action text, the following entry is made: "Remote Update failed. Care for material."

5.2.2.4.3 Negative Feedback Report, Status 5

Notifications of status "5" in the UHDALL lead, in the country SAP, to completion of the REMOTE INFORMED action and the construction of a DISP action. In the action text, the following entry is made: "Remote Update canceled by customer. Contact customer for clarification. If necessary, care for material."

5.2.2.5 Transition Scenarios

During the transition time, until all countries are using the new version of the program, the following scenarios are preferably taken into account:

| Scenario | RU Software Version | Update (Report type UC) | Remote Update Possible |
| --- | --- | --- | --- |
| 1 | Old | No | No |
| 2 | Old | Yes | No |
| 3 | New | No | No |
| 4 | New | Yes | Yes |

Preferably only in the case where an update is replaced by the new process, and the country affected by the update is using the new version of the program, can remote updates be performed.

In all other cases, the previous processes preferably continue to be used.

5.2.3 Demands made of the SM-DB 5.2.3.1 Acceptance of Remote Informed from P42

The data file transferred daily from P42, with the feedback reports on update jobs reported back from the country with status 7 to P42 (see 5.2.1.8) should be incorporated into the SM-DB.

5.2.3.2 Performing the Remote Updates

From the SM-DB, via the on-line connection with the particular plant, the attempt is made to perform the update as shown by the update No. This is repeated several times if needed. If three unsuccessful attempts have been made in the transfer of the update to the plant or if one unsuccessful attempt has been made upon installation, then no further attempt is made (status "FAILED"). If the customer refuses the remote update by actuating the "CANCEL" button in the popup, this leads to the discontinuation of the update (status "CANCEL").

5.2.3.3 Feedback Report on Remote Updates to P42

After the conclusion of the remote update activities, the result per system is reported back to the P42. In a daily file transfer (OPENFT), the update results on the update jobs done are sent to P42. This is again done on the net principle; that is, only the change from the previous run is ever transferred. Per notification handled, the following are sent:

Update No. Material No./Serial No. of the equipment. Date and time the remote update was started (transfer) Date and time the remote update ended (installation) remote update status ("OK" vs. "ERROR" vs. "CANCEL")

5.2.4 Demands Made of Web Application IV/UI

The update handling for non-SAP countries is done via the web application "IV/UI". This application is preferably likewise adapted to remote update.

5.2.4.1 Displaying the Remote Capability of a Update

In describing a update in the web application "IV/UI", the "remote-capable update" flag and the category (see 4.2.1.1) are preferably also assessed and displayed. In displaying the individual update sets, "Remote Distribution" (see 5.2.1.2) on the equipment is preferably also taken into account. If the Equi is remote-capable, then the following are true:

If the update is Category 1, the UHDALL status in P42 is preferably left at "space", and the notation "Remote" is preferably made.

If the update is Category 2 or 3, the UHDALL status in P42 is preferably set to 7, "Remote Informed", and the notation "Remote Informed" is preferably made.

Further processing is then done as in SAP countries (see 5.2.1.8).

5.2.4.2 Displaying the OK Case in Remote Update

The new status "8" for a successful remote update feedback report from the SM-DB to P42 (see 5.2.1.9) is preferably displayed and commented on if needed (equivalent to status "1"). This is preferably protected against being overwritten.

5.2.4.3 Displaying the ERROR Case in Remote Update

The new status "9" for an unsuccessful remote update feedback report from the SM-DB to P42 (see 5.2.1.9) is preferably displayed and commented on if needed (equivalent to status "open" material should be stocked).

5.2.4.4 Displaying the CANCEL Case in Remote Update

The new status "5" for an unsuccessful remote update feedback report (since the customer has refused the update) in the SM-DB to P42 (see 5.2.1.9) is preferably displayed and commented on if needed (equivalent to status "3"; customer has refused update; get in touch with customer; if necessary, stock material).

What is claimed is:

1. For use with a system comprising a first server, a second server storing software update history for medical devices located in a plurality of countries, a third server located in a country and storing software update history for medical devices located in that country, and a database storing a plurality of software updates for various medical devices, a method for remote software updating of a medical device, the method comprising:
    (a) sending, from the first server to the second server, a request for a software update for the medical device;
    (b) sending a command, from the second server to the database, to send the software update to the medical device;
    (c) sending the software update from the database to the medical device;
    (d) after an attempt has been made to install the software update in the medical device, sending a message regarding installation of the software update from the medical device to the database; and
    (e) after receiving the message from the medical device, sending a message regarding installation of the software update from the database to the second server and remotely sending a message regarding installation of the software update from the second server to the third server to automatically update the software update history for the medical device in the second and third servers.

2. The method of claim 1, wherein the first server sends the second server a request for a software update for a group of medical devices, and wherein the second server identifies locations of medical devices that belong to the group of medical devices.

3. The method of claim 1 further comprising sending, from the database to the second server, information regarding which medical devices are available for a remote software update.

4. The method of claim 3 further comprising sending, from the second server to the first server, contingent information on those medical devices that are not available for a remote software update.

5. The method of claim 4, further comprising sending, from the second server to the first server, contingent information regarding how those medical devices not available for a remote software update should be updated.

6. The method of claim 1 further comprising accessing the second server with a computer comprising a web browser to obtain information on the installation.

7. A system for remote software updating of a medical device, the system comprising:
    a first server comprising a first storage medium;
    a second server comprising a second storage medium storing software update history for medical devices located in a plurality of countries;
    a third server located in a country, the third server comprising a third storage medium and storing software update history for medical devices located in that country;
    a database comprising a fourth storage medium storing a plurality of software updates for various medical devices; and
    a medical device comprising a fifth storage medium;
    wherein the first server is operative to send a request to the second server for a software update for the medical device;
    wherein the second server is operative to send a command to the database to send the software update to the medical device;

wherein the database is operative to send the software update to the medical device in response to the command;

wherein the medical device is operative to send a message regarding installation of the software update to the database after an attempt is made to install the software update in the medical device;

wherein after the database receives the message from the medical device, the database is operative to send a message regarding installation of the software update to the second server and is operative to remotely send a message regarding installation of the software update to the third server; and wherein the second and third servers are operative to automatically update the software update history for the medical device after the second and third servers receive the messages, respectively, from the database.

8. The system of claim 7, wherein the first server is operative to send the second server a request for a software update for a group of medical devices, and wherein the second server is further operative to identify locations of medical devices that belong to the group of medical devices.

9. The system of claim 7, wherein the database is further operative to send, to the second server, information regarding which medical devices are available for a remote software update.

10. The system of claim 9, wherein the second server is further operative to send, to the first server, contingent information on those medical devices that are not available for a remote software update.

11. The system of claim 9, wherein the second server is further operative to send, to the first server, contingent information regarding how those medical devices not available for a remote software update should be updated.

12. The system of claim 7 further comprising a computer comprising a web browser operative to access the second server to obtain information on the installations.

* * * * *